United States Patent [19]

Barber, Jr. et al.

[11] 4,056,610

[45] Nov. 1, 1977

[54] MICROCAPSULE INSECTICIDE COMPOSITION

[75] Inventors: Loren L. Barber, Jr., Woodbury; Anthony J. Lucas, Oakdale; Richard Y. Wen, New Brighton, all of Minn.

[73] Assignee: Minnesota Mining and Manufacturing Company, St. Paul, Minn.

[21] Appl. No.: 717,170

[22] Filed: Aug. 24, 1976

Related U.S. Application Data

[63] Continuation of Ser. No. 566,287, April 9, 1975, abandoned.

[51] Int. Cl.$^2$ ............................................. A01N 17/08
[52] U.S. Cl. ....................................... 424/32; 424/16; 424/19; 424/174; 424/186; 424/188; 424/194
[58] Field of Search ........................ 424/16, 19, 32–38, 424/174, 186–194

[56] References Cited

U.S. PATENT DOCUMENTS

| | | | |
|---|---|---|---|
| 2,168,064 | 8/1939 | Faloon | 424/174 |
| 3,063,893 | 11/1962 | Goldborg et al. | 424/188 |
| 3,098,000 | 7/1963 | Harrison | 424/174 |
| 3,130,121 | 4/1964 | Rapport | 424/35 |
| 3,264,176 | 8/1966 | Rapport | 424/188 X |
| 3,541,203 | 11/1970 | Fogle et al. | 424/17 |
| 3,560,613 | 2/1971 | Miskus et al. | 424/174 |
| 3,577,515 | 5/1971 | Vandegaer | 424/32 |
| 3,784,684 | 1/1974 | Bossert et al. | 424/37 |
| 3,839,561 | 10/1974 | Bordenca | 424/174 |

OTHER PUBLICATIONS

Miskus et al., J. Agr. Food Chem., 20(2):313–315 (1972) "Stabilization of Thin Films of Pyrethrins and Allethrin".

Primary Examiner—Shep K. Rose
Attorney, Agent, or Firm—Cruzan Alexander; Donald M. Sell; James V. Lilly

[57] ABSTRACT

A microcapsule insecticide composition comprising microcapsules each having a polyurea shell wall including as an integral part of said shell a photostable ultraviolet light absorbent compound with a log molar extinction coefficient of from about 2 to about 5 with respect to radiation having wave lengths in the range of from about 270 to 350 nanometers and a liquid fill capable of slowly permeating the shell and comprising a pyrethroid and a biological synergist therefor.

18 Claims, No Drawings

MICROCAPSULE INSECTICIDE COMPOSITION

This is a continuation of Ser. No. 566,287 filed Apr. 9, 1975, now abandoned.

BACKGROUND OF THE INVENTION

The present invention relates to microcapsule insecticide compositions which are stabilized against environmental degradation.

Pyrethroids, including both the naturally occurring compounds and their synthetically prepared analogs, are a well known class of contact insecticides. They have broad spectrum activity, that is, they are effective in controlling a variety of pests such as houseflies, mosquitoes, cockroaches, etc. They are not harmful to plants, food, animals and humans and are consequently environmentally safe (leaving no harmful residues).

Despite these highly favorable characteristics, pyrethroids have had only limited usefulness because of their relatively short-lived insecticidal activity. This is due to their decomposition into non-active, non-insecticidal products in the presence of oxygen and ultraviolet light. The speed of this decomposition (or environmental degradation) is dependent upon the environment in which the pyrethroids are placed but typically takes place in from several minutes to several hours. Thus the usefulness of pyrethroids as insecticides has been severely limited by their instability.

Encapsulation of a variety of active liquid substances (including dyes, inks, chemical reagents, pharmaceuticals, flavoring materials, pesticides, herbicides and peroxides) has been suggested to preserve them until released by crushing, melting, dissolving or otherwise removing the capsule wall or until release by diffusion is effected (see for example U.S. Pat. No. 3,577,515). This encapsulation per se is not of great help in the delivery of pyrethroids, since they degrade almost as readily inside the capsules as they do unencapsulated.

Various specific attempts have been made to stabilize pyrethroids against environmental degradation. Thus, antioxidants, biological synergists and photostable ultraviolet light absorbent compounds have been added to solutions of the pyrethroids. Various solid carriers have also been used, such as gum arabic, dextrin, gelatin, unvulcanized rubbers, inorganic powders, and other polymeric products. These attempts have been at best only very moderately successful in reducing the degradation by atmospheric oxygen and ultraviolet radiation and extending the insecticidal life of pyrethroids. Furthermore, they leave behind unsightly residues which are difficult to remove. The pyrethroids are also easily dissolved and washed away by water rinsing (e.g. by rain) thereby preventing their timed release.

SUMMARY OF THE INVENTION

In accordance with the present invention there is provided a microcapsule insecticide composition comprising microcapsules each having a polyurea shell including as an integral part of said shell a photostable ultraviolet light absorbent compound having a log molar extinction coefficient of from about 2 to 5 with respect to radiation having wave lengths in the range of from about 270 to 350 nanometers and a liquid fill capable of slowly permeating the shell and comprising a pyrethroid and a biological synergist therefor.

Preferably the entire microcapsule composition consists essentially of 60-90 percent of liquid fill and 40-10 percent of shell wall, the liquid fill comprising 5-40 percent of pyrethroid, 25-50 percent of biological synergist and 20-40 percent of a water-immiscible organic solvent and the shell including as an integral part thereof 0.5-20 percent of photostable ultraviolet light absorbent compound (all percentages being based on the weight of the entire microcapsule composition).

The pyrethroid remains inside the microcapsules while the composition is packaged and in storage, i.e. in a closed container due to the partial pressure of the pyrethroid surrounding the microcapsules. When the product is applied as an insecticide, the pyrethroid, releases slowly (the actual speed of release depending upon the thickness and porosity of the capsule walls). The pyrethroid is chemically stable during storage and after application until it permeates the capsule walls. At that time it becomes available as an insecticide until degraded to an inactive product. Since the fill permeates the shell wall slowly, the microcapsule product has a long effective insecticidal life and may be stored for extended periods (e.g. for 6 months and more).

The invention also provides a process for controlling insect pests activity by contacting said insects with an effective level of the compositions of the present invention. Contact may be accomplished directly, for example, by atomization of the composition into the air in the form of a spray so that it contacts the insect directly or indirectly by applying the composition to surfaces upon which the insects alight or crawl. Alternatively, compositions of the present invention may be provided in various other forms, for example in sheet materials carrying the microcapsules, (e.g. tapes coated or impregnated with the microcapsules) that may be placed in areas where the insects may alight or crawl. Moreover, animals infested with insects, for example, dogs and cats infested with fleas and poultry infested with lice, can be treated by contacting the fur or feathers of the animal with the compositions of the present invention thereby ending the insect infestation. Other methods of controlling insect activity with formulations of the present invention will be obvious as a result of this disclosure.

DETAILED DESCRIPTION OF THE INVENTION

The microcapsule insecticide compositions of the present invention are conveniently prepared by first dispersing a solution comprising the pyrethroid, the biological synergist, a polyisocyanate and a water-immiscible organic solvent in water by means of agitation and then adding a polyfunctional amine to the water phase while continuing agitation. The microcapsules are formed by interaction between the isocyanate and amine groups at the surfaces of the drops of the disperse phase. An antioxidant and/or a photostable ultraviolet light absorbent compound (sometimes referred to herein as the fill stabilizer) may also be included in the disperse phase solution.

A photostable ultraviolet light absorbent compound having a log molar extinction coefficient of from about 2 to 5 with respect to radiation in the 270 to 350 nanometer wave length range (sometimes referred to herein as the shell stabilizer) is included in the initial charge or is added subsequently (as will be explained) so that it becomes an integral part of the shell wall.

The liquid fill may be prepared by simple admixture of the pyrethroid, the organic solvent, the biological synergist and optionally the antioxidant and/or the fill stabilizer.

There are a number of possible variations in the encapsulation process, although all depend upon the formation of a fine dispersion of the liquid fill (containing the polyisocyanate) in water, for example by means of a high shear mixing apparatus (e.g. a blender). A suspending aid (e.g. the partially neutralized salt of polyacrylic acid such as sodium or potassium polyacrylate or sodium or potassium polymethacrylate) is employed to prevent agglomeration of the droplets of liquid fill. When the dispersion has been established, a polyfunctional amine (preferably from about 0.5 to 3 amine equivalents per isocyanate equivalent, each primary or secondary amine group being theoretically equivalent to one isocyanate group) is preferably added slowly and an organic polyurea microcapsule shell wall forms around each droplet of liquid fill. The shell wall is insoluble in the liquid fill and the water thereby isolating the liquid fill from the external environment. It does, however, allow the pyrethroid to permeate it slowly thereby maintaining an effective level of insecticide upon the outer surface of the shell wall for extended periods of time. Typically preparation of the microcapsule compositions is carried out at from about 15°–50° C.

Preferably at least one of the shell wall reactants is more than bifunctional thereby introducing a degree of crosslinking into the shell wall. However, bifunctional reactants (e.g. toluene diisocyanate and ethylene diamine) may also be used thereby resulting in a shell wall containing essentially no crosslinking. Generally the greater the degree of crosslinking in the shell wall, the less permeable the shell wall is to the pyrethroid.

The microcapsules obtained comprise a distribution of spherical capsules generally ranging from about 1 to 100 microns, and preferably from about 1 to 30 microns, in diameter. Microcapsules having a narrow distribution of diameters may be obtained by adding the polyfunctional amine slowly, preferably in the form of an aqueous solution. Larger and smaller capsules may also be obtained, the larger capsules being produced by low shear and vice versa.

The shell stabilizer is an essential part of the final microcapsule composition and is an integral part of the polyurea shell wall. This may be accomplished by a variety of chemical or physiochemical methods. For example:
1. Reacting the shell stabilizer with available primary, secondary, or tertiary amine groups on the shell wall by adding it to the dispersion of the microencapsulated insecticide composition.
2. Prereacting the polyfunctional amine with the shell stabilizer. The resulting modified polyfunctional amine is added to the dispersion of liquid fill containing the polyisocyanate and a polyurea microcapsule shell wall forms around each droplet of liquid fill.

Suitable shell stabilizers for processes 1 and 2 contain acidic reactive groups. The amount of amine functions added in each case is preferably from about 1.1 to 3 amine equivalents per isocyanate equivalent so that there will be excess amine available for reaction with the shell stabilizer (which takes about 5 minutes).

3. Reacting the polyisocyanate with the shell stabilizer before the polyisocyanate is included in the liquid fill which is dispersed and reacted with a polyfunctional amine to form the polyurea shell wall.

Suitable shell stabilizer for process 3 contain active hydrogen. The amount of amine functions added in this case is preferably from about 0.5 to 3 amine equivalents per isocyanate equivalent.

4. The shell photostabilizer may also be pjysicochemically included in the shell wall by reacting an amine with a shell stabilizer compound and the resultant modified amine coated onto a microencapsulated insecticide composition.
5. Another method of physicochemical inclusion involves coating a microencapsulated insecticide composition with polymeric materials and inorganic sols.

During microencapsulation and incorporation of the shell stabilizer the pH of the dispersion of the reaction mixture is maintained at from about 7–8 to enable the suspending aid to prevent agglomeration of the droplets and the microcapsules.

Suitable pyrethroids for use in the liquid fill include both the naturally occurring pyrethrum esters derived from the dried flower heads of *Chrysanthemum cinerariaefolium* and *Chrysanthemum coccineum* and the synthetically prepared esters of chrysanthemic acid. Naturally occurring pyrethrum esters comprise the group including pyrethrin I, pyrethrin II, cinerin I, cinerin II, and jasmolin II. Synthetically prepared esters comprise the group including allethrins, barthrin, dimethrin, resmethrin, and tetramethrin. The pyrethroids used in the liquid fill may comprise any of the naturally occurring pyrethroids, any of the synthetically prepared pyrethroids, or combinations of two or more of either or both types. A solution of a combination of naturally occurring pyrethroids in deodorized kerosene which is commercially available under the trade designation "Premium Pyrocide 175" from McLaughlin Gormley King Co. of Minneapolis, Minnesota is suitable for use in the present invention.

The synthetic pyrethroids in pure form are crystalline materials which are capable of being dissolved in water immiscible organic solvents. Thus the microcapsule compositions of the invention may include up to 40 percent by weight or even more of the pyrethroid. Ordinarily the compositions contain at least about 5 percent of pyrethroids since lesser amounts thereof result in products of unnecessarily low insecticidal activity. Preferably the microcapsule compositions contain from about 5 to 15 percent (by weight) of pyrethroids.

Suitable biological synergists for inclusion in the liquid fill generally have little or no insecticidal activity by themselves but significantly increase the insecticidal activity of the pyrethroids when combined therewith. A variety of synergists are useful in compositions of the present invention. Representative examples of these synergists are given on pages 196–197 of *Pyrethrum the Natural Insecticide*, edited by John E. Casida, Academic Press, New York and London, 1973. Among the preferred biological synergists are the piperonyl alkyl ethers such as 3, 4-methylenedioxy-6-propylbenzyl butyldiethylene glycol ether (also known as piperonyl butoxide), commercially available under the trade designation "Butacide" from Niagra Chemical Division of FMC Corp. and N-(2-ethylhexyl)-bicyclo[2.2.1]-5-heptene-2,3-dicarboximide commercially available under the trade designation "MGK-264" from the McLaughlin Gormley King Co. of Minneapolis, Minnesota.

The shell stabilizers that are included as an integral part of the shell wall have log molar extinction coefficients of from about 2 to 5 with respect to radiation having wave lengths of from about 270 to 350 nanometers but only minimal absorption in the visible portion of the spectrum. The shell stabilizers are chemically and/or physicochemically bonded or held in or on the shell wall thus forming an integral part thereof. The particular type of shell stabilizing compound used will depend upon the manner in which it is incorporated as will become clear. Thus when the shell stabilizer is chemically bonded in or on the shell wall it will include one or more photostable ultraviolet light absorbent moieties (R') and one or more groups reactive with isocyanate or amine (Q). Thus R' may include, for example, benzophenone, substituted benzophenone, benzotriazole, phenyl salycilate, etc. groups. When Q is reactive toward isocyanate it will contain active hydrogen (e.g. OH present in primary, secondary, or tertiary alcohols,

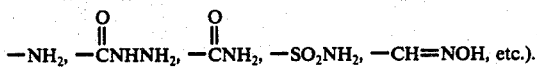

When Q is reactive towards amine it will contain acidic groups having a dissociation constant of at least about $1 \times 10^{-6}$ and includes among others, carboxylic and sulfonic acid groups. A preferred class of shell stabilizers comprises substituted benzophenone sulfonic acids, particularly 2-hydroxy-4-methoxybenzophenone-5-sulfonic acid.

Compounds suitable as the shell stabilizers that are physicochemically held on the shell wall include interpolymers of vinyl compounds and unsaturated dicarboxylic acids reacted with hydroxybenzophenones (such as those described in U.S. Pat. No. 3,393,990) and inorganic sols, e.g. sols of $Fe_2O_3$, $Cr_2O_3$, $TiO_2$, $Al_2O_3$, etc.

The shell stabilizer may comprise from about 0.5 to 20 percent by weight of the microcapsule composition. Preferably it comprises from about 8 to 10 percent by weight of the microcapsule composition.

Suitable water immiscible organic solvents for use in the liquid fill include a wide variety of materials conventionally employed in insecticidal formulations. Preferably the solvent is inert, that is, it is incapable of undergoing chemical reaction with the pyrethroid or any other components of the fill under ambient storage or end use conditions. Also, the solvent is, preferably, one that will not be harmful to the environment in which it is used.

Representative examples of organic solvents useful in the liquid fill include liuid aliphatic hydrocarbons such as pentane, nonane, and decane and their analogs and liquid aromatic hydrocarbons such as benzene, toluene, xylene, etc. Commercially advantageous liquid hydrocarbon products useful in the liquid fill include oils produced from the distillation of coal and the distillation of various types and trades of petroleum stocks. Representative examples of these oils include kerosene, liquid paraffin, paraffin oil, light mineral oil and white mineral oil. Still other solvents useful in the liquid fill include aromatic and aliphatic esters, higher aldehydes, and higher ketones. An especially preferred organic solvent for use in the present invention is deodorized kerosene.

Suitable polyisocyanates for use in the present invention have an isocyanate equivalent weight in the range of from about 70 to 400, and may be represented by the general formula $R(NCO)_n$ wherein R is alkyl, cycloalkyl, aryl, aralkyl or alkaryl and $n$ may be as hight as 10 but is preferably 2 to 3. A preferred sub-class are those containing 2 isocyanate groups. The polyisocyanates are substantially insoluble in water but are readily soluble in the solvent used in the liquid fill. Representative examples of polyisocyanates useful in the present invention include hexamethylene diisocyanate, 1,4-cyclohexane diisocyanate, methylene-bis-4,4-cyclohexylisocyanate, isopropylidene-bis-4,4'-cyclohexylisocyanate, dimer diisocyanate (an isocyanate of the formula OCN-D-NCO wherein D is a $C_{36}$ aliphatic moiety and is commercially available as "DDI" from General Mills), methane diisocyanate, and isophorone diisocyanate. Representative examples of still other useful polyisocyanates include m-phenylene diisocyanate, mixtures of toluene-2,4-diisocyanate and toluene-2,6-diisocyanate, diphenyl-3,3'-dimethyl-4,4'-diisocyanate, diphenyl-3,3'-dimethoxy-4,4'-diisocyanate, diphenylmethane-4,4'-diisocyanate, diphenylmethane-4,4'-dimethyl-3,3'-diisocyanate, 1,5-napthalene diisocyanate. The so-called polymeric polyisocyanates can also be used, such as those obtained by phosgenation of polyamines, prepared by condensing formaldehyde with aromatic amines. Particularly useful polymeric polyisocyanates are the polymethylene polyphenyl polyisocyanates having an average of from about 2 to 2.8 isocyanate groups per molecule such as those sold commercially under the trade designations "Mondur" MR and MRS, (available from Mobay Co.), "Isonate" 901 and 390 P and "PAPI" (available from Upjohn). Lists of commercially available polyisocyanates are found in Kirk and Othmer, *Encyclopedia of Chemical Technology*, Vol. 12, 2nd Ed., pp. 46–47, Interscience Publishers (1967), and Appendix A of Saunders and Frisch, *Polyurethanes: Chemistry and Technology*, Part I, Interscience Publishers, New York (1962); and the polyisocyanate materials therein described can be used in this invention.

Preferably the polyisocyanate comprises from about 5 to 20 percent by weight of the microcapsule composition. An especially preferred polyisocyanate is "Mondur" MRS, a poly (methylenephenylene isocyanate) having a molecular weight of about 380 and an average isocyanate equivalent weight of 133 (thus containing about 2.6 isocyanate groups per molecule). When "Mondur" MRS is used at least a part of the water immiscible organic solvent is aromatic. The biological synergists (e.g. piperonyl butoxide) are aromatic in nature and thus may serve as the aromatic solvent.

Suitable polyfunctional amines for use in the present invention have at least two primary or secondary amine groups per molecule and have an amine equivalent weight in the range of from about 30 to 400. Additionally, the polyfunctional amines are readily soluble in water and preferably are substantially insoluble in the solvent used in the liquid fill. Generally they are selected as water soluble per se. However, they may also be selected as the water soluble salts thereof. Useful polyfunctional amines include aromatic and aliphatic amines. The aromatic amines preferably contain only hydrogen, carbon, nitrogen, and oxygen and the primary amine functions are preferably bonded directly to 6-membered aromatic carbocycles therein. The aliphatic amines preferably are hydrocarbon amines containing up to about 36 carbon atoms. Representative examples of useul polyfunctional amines include ethylene diamine, diethylene triamine, tetraethylene pentamine, hexamethylene diamine, pentaethylene hexamine, polyethylene imine, 2,2'-diaminodiethylether, 1,4-diaminocyclohexane, phenylene diamines (especially m-phenylene diamine), toluene diamine, and melamine. Other amines of the type described are known to the art and are also useful in the present invention. Preferably the polyfunctional amines comprise from about 1 to 10 percent by weight of the microcapsule composition.

Antioxidants may also be included in the liquid fill to minimize the degradative effects of oxygen by inhibiting the formation of hyperoxide groups and their subsequent decomposition into alkoxy and hydroxy radicals in the compositions to be protected. Preferably the antioxidants do not exhibit any substantial chemical reaction with the isocyanate and primary amine groups of the shell forming compounds during the microencapsulation process. A variety of antioxidants are useful in compositions of the present invention. Representative examples include alkylated phenols such as 2,6-di-t-butyl cresol, 2,2'-methylene bis(6-t-butyl-4-methyl phenol), 2,2'-thio bis(6-t-butyl-4-methyl phenol), pentaerythritol tetrakis [3-(3,5-di-tert butyl-4hydroxyphenyl)] propionate, octadecyl 3-(3',5'-di-t-butyl-4'-hydroxyphenyl) propionate commercially available under the trade designation of "Irganox 1076" from Ciba Geigy Corp., etc.; thioesters such as dilauryl thiodipropionate, dimyristyl thiodipropionate; and phospites such as tris (nonylphenyl phosphite). The antioxidants preferably comprise up to 10 percent, and more preferably from about 0.01 to 2 percent, by weight of the microcapsule composition.

Suitable fill stabilizers absorb ultraviolet radiation in the range of about 270-350 nanometers and convert it to a harmless form. They have a high absorption coefficient in the near ultraviolet portion of the spectrum (e.g. a log molar extinction coefficient of from about 2 to 5) but only minimal absorption in the visible portion of the spectrum. Preferably they do not exhibit any substantial chemical reaction with the isocyanate groups and primary amine groups of the shell forming compounds during the microencapsulation process. Among the compounds which can be used as fill stabilizers are substituted benzophenones such as 2,4-dihydroxy benzophenone, 2-hydroxy-4-methoxy benzophenone, 2-hydroxy-4-octyloxy benzophenone, etc.; the benzotriazoles such as 2-(2-hydroxy-5'-methylphenyl) benzotriazole, 2-(3',5'-diallyl-2'-hydroxylphenyl)benzotriazole, etc.; substituted acrylates such as ethyl 2-cyano-3,3-diphenyl acrylate, 2-ethylhexyl-2-cyano-3,3-diphenyl acetate, etc.; salicylates such as phenyl salicylates, 5-butyl phenyl salicylate, etc.; and nickel organic compounds such as nickel bis (octylphenol) sulfide, etc. Additional examples of each of these classes of fill stabilizers may be found in Kirk-Othmer, *Encyclopedia of Chemical Technology*, Second Edition, Volume 21, Interscience Publishers (1970). The fill stabilizers may comprise up to 5 percent, and preferably from about 0.01 to 2 percent, by weight of the microcapsule composition.

The sustained release characteristics and insecticidal lifetime of compositions of the present invention are determined by measuring their biological activity, that is, by determining the percentage of houseflies (*Musca domestica*) that are knocked down after various lengths of exposure to the composition. As the biological activity of an insecticide decreases, more exposure time is necessary in order to obtain a given percent knockdown. Knockdown is defined to mean a condition of paralysis and immobilization typically characterized by the insect lying on its back with, at most, intermittent bursts of uncontrolled kicking and spinning motion or sporadic crippled and unsuccessful attempts at crawling with little or no takeoff or flight.

Biological activity is determined by means of a bioassay test performed both initially (e.g. before the insecticide composition is exposed to simulated outdoor conditions) and after the insecticide composition is exposed to simulated outdoor conditions. In performing the bioassay test, specimens of the insecticide composition to be tested are placed in quart (0.95 liter) glass containers fitted with fine mesh screen tops together with 15-20 houseflies from 1 to 7 days old, and usually from 2 to 5 days old. The percentage of flies knocked down after 15, 30 and 60 minutes of exposure to the specimens is then recorded.

Outdoor conditions are simulated by coating the insecticide composition to be tested onto 62.5 cm × 43.8 cm sheets of polyester film and air drying them at about 27° C for 16 to 24 hours. Polyvinyl alcohol (10 percent or less by weight) may be used as a binder for compositions. The specimens are then exposed to ultraviolet light for varying lengths of time in the wavelength range of from about 270 to about 400 nanometers emitted from a General Electric 275 watt sun lamp. The sun lamp is positioned about 42 cm away from the specimens, resulting in exposure of the insecticide composition to a surface temperature of 30°-40° C and to light having an intensity of from 1800-2200 microwatts/square centimeter.(light intensity of about 1100 microwatts/square centimeter is available outdoors on a clear, sunny summer day at 40° north latitude.)

It has been found that when tested according to this procedure, microcapsule compositions of the present invention that have as little as about 0.007 mg of pyrethroid per square centimeter of polyester and as little as about 0.005 mg of shell stabilizer per square centimer, have long-lived insecticidal activity.

The following examples are meant to further illustrate, but not limit, the present invention. All formulae are given in parts and percentages by weight unless otherwise noted.

Example 1

36.7 parts of a 20% by weight solution of naturally occurring pyrethroids in deoderized kerosene ("Premium Pyrocide 175"[(1)], 36.7 parts of biological synergist (piperonyl butoxide), 0.73 parts of fill stabilizer (4-dodecyloxy-2-hydroxybenzophenone), 0.73 parts of antioxidant (2,6-dioctadecyl-p-cresol) and 14.6 parts of polyisocyanate ("Mondur" MRS[(2)]) are mixed to form a liquid fill composition.

1. Commercially available from McGlaughlin Gormley King Co.
2. Commercially available from Mobay Chemical Co.

A water solution is prepared by adding 54 parts of 17% aqueous polyacrylic acid to 1500 parts of water. The resulting solution is adjusted to a pH of about 7 to 9 with 60 parts of 1N sodium hydroxide.

The liquid fill (including the polyisocyanate) is then dispersed in the water solution in a mixer (a "Dispersator" available from the Premier Mill Corporation) operated at 3000 rpm. After 5 minutes of mixing, 1.5 parts of polyfunctional amine (tetraethylene pentamine) are added over approximately 2.5 minutes. The resulting mixture is allowed to react for five minutes at room temperature (approximately 25° C) at 3000 rpm. while the microcapsule shell walls form. A shell stabilizer (9.04 parts of 2-hydroxy-4-methoxy-benzophenone-5-sulfonic acid) is added to the dispersion of microcapsules over a 2 minute period and reacted with the available amine groups of the shell wall. The reaction takes 3–5 minutes and goes to completion. The pH of the composition is maintained at 7–9 by the addition of sodium hydroxide.

The resulting composition comprises microcapsules (10–30 microns in diameter) each having a polyurea shell containing a photostable ultraviolet light absorbent compound (a shell stabilizer) as an integral part thereof and a liquid fill comprising a natural pyrethroid, an organic solvent, a biological synergist, an antioxidant, and a photostable ultraviolet light absorbent compound (a fill stabilizer). The composition is then coated onto polyester, as described above, at three different coating weights. The first coating has a pyrethroid concentration of 0.105 mg/cm$^2$ and a shell stabilizer concentration of 0.0775 mg/cm$^2$ on the polyester. The second coating has a pyrethroid concentration of 0.102 mg/cm$^2$ and a shell stabilizer concentration of 0.170 mg/cm$^2$, and the third a pyrethroid concentration of 0.093 mg/cm$^2$ and a shell stabilizer concentration of 0.294 mg/cm$^2$ on the polyester. The samples are then tested for biological activity both initially and after exposure to 88 hours of simulated outdoor conditions. In all instances, each sample knocks down 100 percent of the houseflies within 15 minutes.

The unencapsulated liquid fill used in this example is coated onto polyester to a pyrethroid concentration of 0.22 mg/cm$^2$. The sample is tested for biological activity both initially and after 30 hours of exposure to stimulated outdoor conditions. It initially knocks down 100 percent of the houseflies within 15 minutes initially but after 30 hours of exposure to simulated outdoor conditions, it knocks down 0 percent of the houseflies within 60 minutes.

A microcapsule insecticide composition similar to the above-described microcapsule composition but containing no shell stabilizer is coated onto polyester to a pyrethroid concentration of 0.11 mg/cm$^2$. The sample is tested for biological activity both initially and after exposure to 39 hours of simulated outdoor conditions. It initially has 100 percent knockdown of the houseflies within 15 minutes. After exposure to 39 hours of simulated outdoor conditions, it knocks down 0 percent of the houseflies within 60 minutes.

EXAMPLE 2

85 parts of polyisocyanate ("Mondur" MRS) are reacted for 30 minutes with 15 parts of a shell stabilizer (2-amino-5-chlorobenzophenone) to form a modified polyisocyanate. The reaction takes place at room temperature (25° C) with mild agitation.

A liquid fill is prepared by mixing 35.1 parts of pyrethroid solution ("Premium Pyrocide 175"), 35.1 parts of biological synergist (piperonyl butoxide), 7.1 parts of antioxidant (2,6 di-t-butylcresol) and 3.2 parts of fill stabilizer (4-dodecyloxy-2-hydroxybenzophenone). 16.2 parts of the modified polyisocyanate are then added to the liquid fill.

A water solution is prepared and the liquid containing the modified polyisocyanate is dispersed therein as described in Example 1. After 5 minutes of mixing, 2.6 parts of polyfunctional amine (diethylenetriamine) in 2.6 parts of water are added over approximately 5 minutes. The resulting mixture is allowed to react as described in Example 1 while the microcapsule shell wall forms.

The resulting composition comprises microcapsules (1–25 microns in diameter) each having a polyurea shell containing a shell stabilizer as an integral part thereof and a liquid fill comprising a natural pyrethroid, an organic solvent, a biological synergist, an antioxidant, and a fill stabilizer. The composition is then coated onto polyester, as described above, to a pyrethroid concentration of 0.102 mg/cm$^2$ and a shell photostabilizer concentration of 0.102 mg/cm$^2$.

The samples are then tested for biological activity both initially and after exposure to 41 hours of simulated outdoor conditions. The sample initially has 100 percent knockdown of the houseflies within 15 minutes and 100 percent knockdown within 60 minutes after 41 hours of exposure to simulated outdoor conditions.

EXAMPLE 3

30.8 parts of pyrethroid solution ("Premium Pyrocide 175"), 30.8 parts of biological synergist (piperonyl butoxide), 0.7 parts of fill stabilizer (4-dodecyloxy-2-hydroxybenzophenone) and 0.7 parts of antioxidant (2,6-dioctadecyl-p-cresol) are mixed to form a liquid fill composition. 12.2 parts of polyisocyanate ("Mondur" MRS) are added to the fill.

A water solution is prepared by adding 54 parts of 17% aqueous polyacrylic acid to 1500 parts of water. The resulting solution is adjusted to a pH of about 7 to 9 with 60 parts of 1N sodium hydroxide.

The liquid fill (including the polyisocyanate) is then dispersed in the water solution in a "Dispersator" operated at 3000 rpm. After 5 minutes of mixing, 2.5 parts of polyfunctional amine (tetraethylene pentamine) are added over approximately 2.5 minutes. The resulting mixture is allowed to react for five minutes at room temperature (approximately 25° C) at 3000 rpm. while the microcapsule shell walls form.

A modified amine is prepared by reacting 15 parts of a shell stabilizer (2-hydroxy-4-methoxybenzophenone-5-sulfonic acid) and 7.3 parts of triethanolamine in 40 parts of water at about 25° c for 5 minutes. The modified amine is then added to the microcapsule composition and mixed therewith for about 5 minutes until it coats the microcapsule shell wall.

The resulting composition comprises microcapsules (1–30 microns in diameter) each having a polyurea shell having a coating with a shell stabilizer physicochemically attached thereto, and a liquid fill comprising a natural pyrethroid, an organic solvent, a biological synergist, an antioxidant and a fill stabilizer. The composition is then coated onto polyester, as described above, to a pyrethroid concentration of 0.179 mg/cm$^2$ and a shell stabilizer concentration of 0.248 mg/cm$^2$.

The composition is tested for biological activity initially and has 100 percent knockdown of the houseflies within 15 minutes. After exposure to simulated outdoor conditions for 80 hours, it provides 100 percent knockdown of the houseflies within 15 minutes. The composition is then stored at room temperature (e.g. 25° C) for 19 days in a glass jar with some of the storage being under normal room fluorescent lighting and some of the storage being in the dark. After this storage, the composition provides 100 percent knockdown of the houseflies within 15 minutes. The composition is then exposed to simulated outdoor conditions for an additional 16 hours (making a total of 96 hours of exposure to simulated outdoor conditions and 19 days of room temperature storage) and provides 100 percent knockdown of the houseflies within 15 minutes. The composition is then stored at room temperature for an additional 165 days (making a total of 96 hours of exposure to simulated outdoor conditions and 184 days of room temperature storage) and provides 100 percent knockdown of the houseflies within 15 minutes.

EXAMPLE 4

A microcapsule insecticide composition according to the present invention is prepared according to the procedures used in Example 3. The liquid fill comprises 22.1 parts of pyrethroid solution ("Premium Pyrocide"), 22.1 parts of biological synergist (piperonyl butoxide), 0.45 parts of antioxidant (2,6 dioctadecyl-p-cresol), 0.45 parts of fill stabilizer (4-dodecyloxy-2-hydroxybenzophenone). 9 parts of polyisocyanate ("Mondur" MRS) are added to the fill. The liquid fill, including the polyisocyanate, is then dispersed in the water solution and 1.8 parts of polyfunctional amine are added. After the formation of the shell, the resulting microcapsules are filtered from the water phase. The filter cake is then diluted with about 450 parts of water and 44.1 parts of $Fe_2O_3$ sol (5.3% $Fe_2O_3$ by weight commercially available under the tradename "LN-1331" from Nalco Chemical Co.) are added to the microcapsule composition and mixed therewith for about 5 minutes until it coats the microcapsule shell wall.

The resulting composition comprises microcapsules (1–40 microns in diameter) each having a polyurea shell having a coating with a shell stabilizer physicochemically attached thereto, and a liquid fill comprising a natural pyrethroid, an organic solvent, a biological synergist, an antioxidant, and a fill stabilizer. The composition is then coated onto polyester, as described above, to a pyrethroid concentration of 0.186 mg/$cm^2$ and a shell stabilizer concentration of 0.99 mg/$cm^2$.

The composition is then tested for biological activity both initially and after exposure to 60 hours of simulated outdoor conditions. The composition initially has 100 percent knockdown of the houseflies within 15 minutes. It provides 100 percent knockdown of the houseflies within 60 minutes after 60 hours of exposure to simulated outdoor conditions.

EXAMPLE 5

A microcapsule insecticide composition according to the present invention is prepared according to the procedures used in Example 1. The liquid fill comprises 37.8 parts pyrethroid solution ("Premium Pyrocide 175"), 37.8 parts biological synergist (piperonyl butoxide), 0.8 parts fill stabilizer (2-hydroxy-4-methoxybenzophenone) and 0.1 parts antioxidant (octadecyl 3-(3',5'-di-t-butyl-4'-hydroxyphenyl)propionate). Eight parts of polyisocyanate ("Mondur" MRS) are added to the liquid fill. The liquid fill, including the polyisocyanate, is dispersed in the water solution and 6 parts of polyfunctional amine (tetraethylene pentamine) dissolved in 4 parts of water are added dropwise over a 2.5 minute period. After the formation of the shell, 9.3 parts of shell stabilizer (2-hydroxy-4-methoxybenzophenone-5-sulfonic acid) in 31 parts of water are added dropwise over a 2 minute period.

The resulting composition comprises microcapsules (8–15 microns in diameter) each having a polyurea shell containing a shell stabilizer as an integral part thereof and a liquid fill comprising a natural pyrethroid, an organic solvent, a biological synergist, an antioxidant and a fill stabilizer. The composition is then sprayed onto a 100 micron thick circular sheet of polyester film measuring 57 square centimeters in area. The concentration of pyrethrin is 0.0075 mg/$cm^2$. The concentration of second photostable compound is 0.009 mg/$cm^2$.

The composition is tested for biological activity against German cockroaches both initially and after exposure to simulated outdoor conditions for 16 hours. The sprayed test sample is placed on a flat surface with the sprayed side up. A test cylinder measuring 7.5 centimeters in height by 8.52 cm in diameter is placed over the test sample. The interior walls of the test cylinder are coated with petroleum jelly followed by talc. Five German cockroaches that have been starved for one week are placed into the test cylinder and their knockdown is observed. The composition initially has 100 percent knockdown of the cockroaches within 20 minutes. The composition has 100 percent knockdown of the cockroaches within 30 minutes after exposure to simulated outdoor conditions for 16 hours. When non-encapsulated pyrethroid compositions are subjected to 16 hours of simulated outdoor exposure, they have 0% knockdown of the cockroaches within 30 minutes.

EXAMPLE 6

The outdoor photo and thermal stability and weatherability of the composition of Example 2 is measured. Samples of polyester film are coated to a pyrethroid concentration of 0.102 mg/$cm^2$ and a shell stabilizer concentration of 0.102 mg/$cm^2$. The samples are exposed to direct summer sunlight (intensity of about 1100 microwatts/$cm^2$) at an air temperature of from 24° C to 32° C and are then tested for biological activity both initially and after a total outdoor exposure to direct sunlight of 43 hours. The composition provides 100 percent knockdown of the flies within 15 minutes, in both cases.

EXAMPLE 7

300 parts of the composition of Example 3 are diluted with 300 parts of water and placed into a "Jet-Pak" aerosol system (commercially available from Spray-on Products, Inc. of Anaheim, California). The resulting aerosol insecticide composition is compared for biological activity with "Buggy Whip" (commercially available aerosol pyrethrin insecticide available from S.C. Johnson Co. of Racine, Wisconsin) by liberally spraying one surface of separate cardboard panels (3.4 m × 1.7 m) with each of the compositions. The panels have a pyrethroid concentration of about 0.1 mg/$cm^2$ on them. The panel coated with the composition of Example 3 has a concentration of shell stabilizer of about 0.2 mg/$cm^2$ upon it. The coated panels are stored for varying lengths of time under normal office fluorescent lighting at a temperature of 15° C–21° C and a relative humidity of 50%–60%.

Biological activity is tested in a room (4.9 $m$ × 4.6 $m$ × 3.4 $m$) maintained at 15°–29° C and 50–60% relative humidity. The room has fluorescent lighting and one western window. A number of houseflies (e.g. 200–300) are placed in the room approximately one hour before the coated panels are introduced. The knockdown that occurs during this period is recorded. The coated panels are then placed in the room and the knockdown recorded. Panels coated with the composition of Example 3 knockdown 80% of the houseflies within two hours even after having been stored for 1056 hours (44 days). Panels coated with "Buggy Whip" do not knockdown any of the flies within two hours after having been stored for 456 hours (19 days).

EXAMPLE 8

A microcapsule insecticide composition according to the invention is prepared as described in Example 1. The liquid fill comprises 36.2 parts of pyrethroid solution ("Premium Pyrocide 175"), 36.2 parts of biological synergist (piperonyl butoxide), 0.7 parts of fill stabilizer (4-dodecyloxy-2-hydroxybenzophenone), and 0.7 parts of antioxidant (2,6-dioctadecyl-p-cresol). 14.5 parts of polyisocyanate ("Mondur" MRS) are added to the liquid fill. The liquid fill, including the polyisocyanate, is dispersed in the water solution and 2.9 parts of polyfunctional amine (tetraethylene pentamine) are added over a five minute period. After the formation of the shell, 8.9 parts of shell stabilizer (2 hydroxy-4-methoxybenzophenone-5-sulfonic acid) are added over a 2 minute period.

The resulting composition comprises microcapsules (1-30 microns in diameter) each having a polyurea shell containing a shell stabilizer as an integral part thereof and a liquid fill comprising a natural pyrethroid, an organic solvent, a biological synergist, an antioxidant and a fill stabilizer.

Sustained release properties of compositions of the present invention are demonstrated by depositing 15 parts of the dispersion of this example on each of two No. 5 "Whatman" filter papers and washing one of the samples with five successive portions of water (500 parts each) to remove the pyrethroid from the surface of the capsules. Each wash is tested for the presence of pyrethroid by means of ultravoilet spectroscopy. The absence of pyrethroid is discovered in the fifth washing.

The washed and unwashed samples are air dried for 3 hours at 23° C and then tested for biological activity. Both samples knockdown 95% or more of the houseflies within 15 minutes and 100 percent of the flies within 30 minutes. This illustrates that the shell wall is permeable to the liquid fill thereby allowing it to migrate to the outer surface thereof and maintain an effective level of insecticide thereon.

EXAMPLE 9

A microcapsule insecticide composition according to the invention is prepared as described in Example 1. The liquid fill comprises 36.8 parts of synthetic pyrethroid solution ("SBP" 1382[3]), and 36.8 parts of biological synergist (piperonyl butoxide). 14.64 parts of polyisocyanate ("Mondur" MRS) are added to the liquid fill. The liquid fill, including the polyisocyanate, is dispersed in the water solution and 2.94 parts of polyfunctional amine (tetraethylenepentamine) are added over a five minute period. After the formation of the shell, 8.82 parts of shell stabilizer (2 hydroxy-4-methoxy benzophenone-5-sulfonic acid) are added over a 2 minute period.

[3]. A synthetic pyrethroid commercially available from S. B. Penick and Co. of New York, New York and comprising 40% by weight (5-benzyl-3-furyl) methyl-2,2-dimethyl-3-(2-methylpropenyl)cyclopropane-carboxylate and 60% by weight aromatic petroleum hydrocarbons.

The resulting composition comprises microcapsules (1-30 microns in diameter) each having a polyurea shell containing a shell stabilizer as an integral part thereof and a liquid fill comprising a synthetic pyrethroid, an organic solvent and a biological synergist. The composition is coated onto polyester film to a pyrethroid concentration of 0.12 mg/cm[2] and a shell stabilizer concentration of 0.074 mg/cm[2]. The composition is tested for biological activity both initially and after 15 hours of exposure to simulated outdoor conditions. It initially provides 100 percent knockdown of houseflies within 15 minutes. It provides 30 percent knockdown of houseflies within 60 minutes after exposure to simulated outdoor conditions for 15 hours. Unencapsulated synthetic pyrethroid compositions have no biological activity (e.g. 0% knockdown) after 7 hours of exposure to simulated outdoor conditions.

EXAMPLE 10

A microcapsule insecticide composition according to the invention is prepared as described in Example 1. The liquid fill comprises 36.8 parts of pyrethroid solution ("Premium Pyrocide 175"), and 36.8 parts of biological synergist (piperonyl butoxide). 14.64 parts of polyisocyanate ("Mondur" MRS) are added to the liquid fill. The liquid fill, including the polyisocyanate, is dispersed in the water solution and 2.94 parts of polyfunctional amine (tetraethylenepentamine) are added over a five minute period. After the formation of the shell, 8.82 parts of shell stabilizer (2 hydroxy-4-methoxybenzophenone-5-sulfonic acid) are added over a 2 minute period.

The resulting composition comprises microcapsules (1-30 microns in diameter) each having a polyurea shell containing a shell stabilizer as an integral part thereof and a liquid fill comprising a natural pyrethroid, an organic solvent and a biological synergist. The composition is coated onto polyester film to a pyrethroid concentration of 0.76 mg/cm[2] and a second photostable compound concentration of 0.936 mg/cm[2]. The composition is tested for biological activity both initially and after 40 hours of exposure to simulated outdoor conditions. It initially provides 100 percent knockdown of houseflies within 15 minutes. It provides 100 percent knockdown of houseflies within 60 minutes after 40 hours of exposure to simulated outdoor conditions. When the liquid fill of this example is unencapsulated, it has no biological activity (e.g. 0% knockdown) after 20 hours of exposure to simulated outdoor conditions.

What is claimed is:

1. The method of controlling insect pest activity comprising contacting said insects, in an environment having ultra violet light activity degrading to pyrethroid, with a microcapsule insecticide composition comprising microcapsules each having (i) a permeable polyurea shell including as an integral part of said shell a shell stabilizer comprising a photostable ultraviolet light absorbent compound having a log molor extinction coefficient of from about 2 to 5 with respect to radiation having wavelengths in the range of from about 270 to 350 nanometers, and (ii) a liquid fill comprising a pyrethroid, a water-immiscible organic solvent, an antioxidant, a biological synergist for said pyrethroid and a fill stabilizer comprising a photostable ultraviolet light absorbent compound having a log molar extinction coefficient of from about 2 to 5 with respect to radiation having wavelengths in the range of from about 270 to 350 nanometers; wherein said liquid fill permeates said porous polyurea shell over a sustained period of time and maintains an insecticidally effective level of pyrethroid upon the outer surface of the shell wall for an extended period of time.

2. The method according to claim 1 wherein said shell stabilizer comprises a benzophenone substituted with an acidic group having a dissociation constant greater than $1 \times 10^{-6}$.

3. The method according to claim 2 wherein said benzophenone is 2-hydroxy-4-methoxybenzophenone-5-sulfonic acid.

4. The method according to claim 1 wherein said shell stabilizer comprises a benzophenone substituted with a group containing at least one active hydrogen.

5. The method according to claim 4 wherein said benzophenone is 2-amino-5-chlorobenzophenone.

6. The method according to claim 1 wherein said biological synergist is selected from the group consisting of 3,4-methylenedioxy-6-propylbenzyl butyldiethylene glycol ether and N-(2-ethylhexyl)-bicyclo[2.2.1]-5-heptene-2,3-dicarboximide.

7. The method according to claim 1 wherein said antioxidant comprises an alkylated phenol.

8. The method according to claim 7 wherein said alkylated phenol is octadecyl-3-(3',5'-di-t-butyl-4'-hydroxyphenyl)-propionate.

9. The method according to claim 1 wherein said water-immiscible organic solvent is deodorized kerosene.

10. The method according to claim 1 wherein said fill stabilizer comprises a benzophenone.

11. The method according to claim 10 wherein said benzophenone is 4-dodecyloxy-2-hydroxybenzophenone.

12. The method according to claim 1 wherein said composition is applied to a sheet material prior to contacting said insects.

13. The method of controlling insect pest activity comprising contacting said insects, in an environment having ultraviolet light activity degrading to pyrethroid, with a microcapsule insecticide composition comprising microcapsules in the range from about 1 to 100 microns each having (i) a polyurea shell including as an integral part of said shell 2-hydroxy-4-methoxybenzophenone-5-sulfonic acid shell stabilizer and (ii) a liquid fill capable of slowly permeating said shell and comprising a solution of naturally occurring pyrethroids in deodorized kerosene, 3,4-methylenedioxy-6-propylbenzyl butyldiethylene glycol ether synergist, octadecyl-3-(3',5'-di-t-butyl-4'-hydroxyphenyl)propionate antioxidant, and 2-hydroxy-4-methoxybenzophenone fill stabilizer.

14. The method according to claim 1 wherein said shell stabilizer is chemically attached to said permeable polyurea shell wall.

15. The method according to claim 1 wherein said shell stabilizer is physicochemically held on said permeable polyurea shell wall.

16. A microcapsule insecticide composition comprising from about 60–90 percent liquid fill and from about 40–10 percent porous polyurea shell;
   wherein said liquid fill comprises from about
   a. 5–40 percent of pyrethroids selected from the group consisting of pyrethrin I, pyrethrin II, cinerin I, cinerin II, jasmolin II, allethrin, barthrin, dimethrin, resmethrin and tetramethrin;
   b. 20–40 percent of a water-immiscible organic solvent selected from the group consisting of pentane, nonane, decane and their analogs, benzene, toluene, xylene, deodorized kerosene, liquid parafin, parafin oil, light mineral oil and white mineral oil;
   c. 0.01–2 percent of an alkylated phenol antioxidant selected from the group consisting of 2,6-di-t-butyl cresol; 2,2'-methylene-bis-(6-t-butyl-4-methyl phenol); 2,2'-thio bis-(6-t-butyl-4-methyl phenol); pentaerythritol tetrakis-[3-(3,5-di-tert-butyl-4-hydroxyphenyl)]-propionate; 2,6-dioctadecyl-p-cresol and octadecyl-3-(3',5'-di-t-butyl-4'-hydroxyphenyl) propionate;
   d. 25–50 percent of a piperonyl alkyl ether synergist selected from the group consisting of 3,4-methylenedioxy-6-propylbenzyl butyldiethylene glycol ether and N-(2-ethylhexyl)-bicyclo[2.2.1]-5-heptene-2,3-dicarboximide; and
   e. 0.01–2 percent by weight of a benzophenone fill stabilizer selected from the group consisting of benzophenone; 2,4-dihydroxybenzophenone; 2-hydroxy-4-methoxybenzophenone; 2-hydroxy-4-octyloxybenzophenone; and 4-dodecyloxy-2-hydroxybenzophenone; and
   wherein said porous polyurea shell includes, as an integral part thereof, from about 0.5 – 20 percent of 2-hydroxy-4-methoxybenzophenone-5-sulfonic acid as a shell stabilizer; and
   wherein said liquid fill permeates said porous polyurea shell wall over a sustained period of time and maintains an insecticidally effective level of pyrethroid upon the outer surface of said shell wall for an extended period of time in an environment having ultra violet light activity normally degrading to pyrethroid; and
   wherein all percentages are percentages by weight of said microcapsule insecticide composition.

17. A microcapsule insecticide composition according to claim 16 wherein said microcapsules are in the range of about 1 to 100 microns each and wherein said pyrethroids are selected from the group consisting of pyrethrin I, pyrethrin II, cinerin I, cinerin II and jasmolin II.

18. A microcapsule composition comprising about 25 percent porous polyurea shell wall and about 75 percent liquid fill;
   wherein said permeable shell comprises about 16 percent porous polyurea and 9 percent 2-hydroxy-4-methoxybenzophenone-5-sulfonic acid as an integral part thereof; and
   wherein said liquid fill comprises about 36.9 percent of a solution of naturally occurring pyrethroids in deodorized kerosene, about 36.9 percent 3,4-methylenedioxy-6-propylbenzylbutyldiethylene glycol ether, about 0.7 percent 2,6-dioctadecyl-p-cresol and about 0.7 percent 4-dodecyloxy-2-hydroxybenzophenone;
   wherein said liquid fill permeates said porous polyurea shell over a sustained period of time and maintains an insecticidally effective level of pyrethroid upon the outer surface of said shell wall for an extended period of time in an environment having ultraviolet light activity degrading to pyrethroids; and
   wherein all percentages are percentages by weight of said microcapsule insecticide composition.

* * * * *